United States Patent [19]

Hayashi et al.

[11] 4,054,736

[45] Oct. 18, 1977

[54] CLATHRATE COMPOUNDS OF PROSTAGLANDINS OR THEIR ANALOGUES WITH CYCLODEXTRIN

[75] Inventors: Masaki Hayashi, Takatsuki; Atsunobu Ishihara, Ibaraki, both of Japan

[73] Assignee: Ono Pharmaceutical Co., Ltd., Osaka, Japan

[21] Appl. No.: 421,795

[22] Filed: Dec. 5, 1973

Related U.S. Application Data

[63] Continuation-in-part of Ser. No. 286,731, Sept. 6, 1972, abandoned, which is a continuation-in-part of Ser. No. 147,255, May 26, 1971, Pat. No. 3,816,393.

[30] Foreign Application Priority Data

June 10, 1970   Japan .................................. 45-50119

[51] Int. Cl.$^2$ ............................................. C08B 37/16
[52] U.S. Cl. ....................................... 536/103; 424/361
[58] Field of Search ........................ 260/209 R, 209 D; 536/103

[56] References Cited

U.S. PATENT DOCUMENTS 3,816,393   6/1974   Hayashi et al. .................. 260/209 R

*Primary Examiner*—Johnnie R. Brown
*Attorney, Agent, or Firm*—Bierman & Bierman

[57] ABSTRACT

Clathrate compounds of prostaglandins or their analogues with cyclodextrins and a method of manufacture thereof. The compounds are useful as labor inducing agents, contraceptives, hypotensives and remedies for ulcers and asthma.

21 Claims, No Drawings

CLATHRATE COMPOUNDS OF PROSTAGLANDINS OR THEIR ANALOGUES WITH CYCLODEXTRIN

This application is a continuation-in-part of application Ser. No. 286,731, filed Sept. 6, 1972, now abandoned, which is a continuation-in-part of application Ser. No. 147,255, filed May 26, 1971, which claims the priority of Japanese 50119/70 filed June 10, 1970, 1 now U.S. Pat. No. 3,816,393.

This invention relates to clathrate compounds of prostaglandins or their analogues with cyclodextrin. It also relates to a process for producing clathrate compounds of prostaglandins or their analogues with cyclodextrin, characterized by reacting prostaglandins or their analogues with cyclodextrin. Further the present invention relates to the use of clathrate compounds of prostaglandins or their analogues with cyclodextrin in pharmaceutically useful forms.

A prostaglandin group of compounds exists in various tissues of animals and is noted as a new hormone which is secreted by the living body itself and gives effects on blood pressure, smooth muscle, lipid metabolism, platelet aggregation, gastric secretion and the like at a slight dose.

"Prostaglandin" is a general term for a group of compounds which contain the carbon skeleton of prostanoic acid. As primary compounds among them, there may be mentioned prostaglandin $E_1$ (hereinafter referred to as $PGE_1$), prostaglandin $E_2$ (hereinafter referred to as $PGE_2$), prostaglandin $A_1$ (hereinafter referred to as $PGA_1$), prostaglandin $A_2$ (hereinafter referred to as $PGA_2$), prostaglandin $F_1\alpha$(hereinafter referred to as $PGF_{1\alpha}$), prostaglandin $F_2\alpha$(hereinafter referred to as $PGF_{2\alpha}$), 15-methyl prostaglandin $E_1$ (hereinafter referred to as 15-methyl $PGE_1$), 16-methyl prostaglandin $E_1$ (B) (hereinafter referred to as 16-methyl $PGE_1$ (B) ), and 17-methyl prostaglandin $E_1$ (B) (hereinafter referred to as 17-methyl $PGE_1$, (B) ), which naturally occur in the living body and have potensive pharmacological activities. The structural formula of prostanoic acid is as follows:

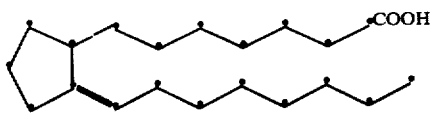

These compounds are useful as hypotensive agents, remedies for gastric ulcer, contaceptives, labor-inducing agents, anti-thrombotic agents and remedies for asthma. Thus, more particularly, $PGE_1$ and $PGE_2$ are useful as hypotensive agents, remedies for gastric ulcer, remedies for asthma, contraceptives and labor-inducing agents. $PGE_1$ is also useful as an anti-thrombotic agent, $PGF_{1\alpha}$ and $PGF_{2\alpha}$ as contraceptives and labor-inducing agents and $PGA_1$ and $PGA_2$ as hypotensive agents.

Further, the compounds containing carbon skeletons similar to that of prostanoic acid have biological activities as well as the prostaglandins and some of them exert much better effects than prostaglandins. For example, the compound with a methyl group in the C-15, C-16 or C-17 position usually has greater duration and potensive activity compared with the corresponding prostaglandin. ω-Homo $PGE_1$ is better for inhibiting platelet aggregation than $PGE_1$. In case functional group of prostaglandins or compounds containing the carbon skeletons similar to that of prostanoic acid are substituted by other functional group, the resulting compounds also have excellent effects. For example, $PGE_2$ decyl ester shows a duration in gastric secretion inhibiting effect and when used in therapy for gastric ulcer, its side effect, that is, hypertensive effect and smooth muscle contracting effect are far weaker than $PGE_2$. Further, $PGE_2$-9-carboethoxy nonyl ester shows more potensive effect than $PGE_2$ in therapy for asthma.

As mentioned above, prostaglandins and their analogues are remedies for various diseases but they are unstable so that there is difficulty in applying them in pharmaceutically satisfactory forms. Among the naturally occurring prostaglandin group of compounds, the PGE group is most unstable because the OH group of the 5 membered ring is easily eliminated under the influence of the C-9 carbonyl group as shown by the following formula:

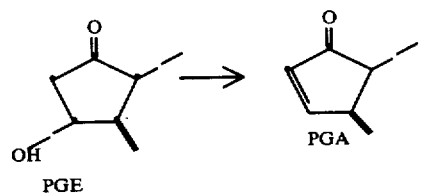

The elimination of the OH group results in the formation of prostaglandin A containing a couble bond in the ring. Furthermore, PGE analogues have the same tendency as PGE compounds.

The other prostaglandins and their analogues are also unstable compared with other drugs because of the presence of double bonds or OH groups in their structures.

By reacting prostaglandin analogues with various host molecules, we investigated the structures and stabilities of the resulting products, i.e. clathrate compounds. As a result, we have found that cyclodextrin clathrate compounds are obtained as white powdery substances when cyclodextrin is used for the host molecule and that each of the resulting clathrate compounds is highly stable.

The above finding is unexpected because the urea or thiourea is used for a host molecule, prostaglandins or their analogues do not form the clathrate compounds therewith. Clathrate compounds of urea, cyclodextrin or the like have been used hitherto in order to stabilize various substances. However, that is because clathrate compounds are considered to be effective in preventing photo-oxidate decomposition of a double bond or the like, but the fact that cyclodextrin clathrate compounds effectively prevent the elimination of OH group as in this invention has never been known.

Prostaglandin or analogues thereof to be employed in producing cyclodextrin clathrate compounds according to this invention are those which contain the carbon skeleton of prostanoic acid or one similar to that of prostanoic acid. The prostaglandins or their analogues may have a methyl group introduced on the side chain. Further, carboxylic acid moiety in the prostaglandins or analogues thereof may be in the form of ester with a rather bulky substituent group.

Among the cyclodextrins, α-cyclodextrin or γ-cyclodextrin, like β-cyclodextrin, can form clathrate compounds with prostaglandins or their analogues. As with β-cyclodextrin, the thus-obtained clathrate compounds have much better stability than the non-clathrate initial prostaglandins or their analogues. Mixtures of these cyclodextrins are also suitable.

In preparing the clathrate compounds, cyclodextrin dissolved in water or in an organic solvent miscible with water is added to a prostaglandin analogue compound dissolved in an organic solvent which is miscible with water. After the mixture is heated, the desired product is obtained by concentrating the mixture under reduced pressure or leaving it to be cooled. In this case, the mixing ratio of organic solvent with water may be suitably varied according to the solubilities of the starting materials and products. Due to the low thermostabilities of the host molecules, it is preferable that this reaction is conducted at a temperature below 70° C. Especially in the case of PGE or its analogues, it is preferable to conduct the reaction at a temperature of 20°–60° C.

The process for producing the clathrate compounds will be illustrated by the following examples and the results of heat stability tests on these compounds are to be found in Table 1.

EXAMPLE 1

350 mg. of β-cyclodextrin was dissolved in 4.7 ml. of water and the solution was added to 21.4 mg. of $PGE_2$ dissolved in 0.3 ml. of ethanol. After the mixture was heated to dissolve at 60° C., it was cooled slowly to room temperature, to obtain a precipitate. After having left to stand overnight at room temperature, the precipitate was recovered by filtration and washed with 50% aqueous ethanol and dried under reduced pressure to obtain 300 mg. of desired product. The content of $PGE_2$ in the product was 4.7%.

EXAMPLE 2

A solution prepared by heating and dissolving 523 mg. of β-cyclodextrin in 4.7 ml. of water was added to a solution prepared by dissolving 20.9 mg. of $PGE_2$ decyl ester in 2.8 ml. of ethanol. The mixture was heated to dissolve at 60° C. and then treated in the same manner as in Example 1 to obtain the desired product. The yield was 180 mg. The content of $PGE_2$ decyl ester in the product was 9.4%.

EXAMPLE 3

A solution prepared by heating and dissolving 480 mg. of 62 -cyclodextrin in 4.7 ml. of water was added to a solution prepared by dissolving 21.7 mg. of $PGE_1$ decyl ester in 2.8 ml of ethanol. The mixture was heated to dissolve at 60° C. and then treated in the same manner as in Example 1 to obtain the desired product. The yield was 210 mg. The content of $PGE_1$ decyl ester was 7.9%.

EXAMPLE 4

A solution prepared by heating and dissolving 358 mg. of β-cyclodextrin in 4 ml. of water was added to a solution prepared by dissolving 23.8 mg. of $PGA_2$ in 1.0 ml. of ethanol. The mixture was heated to dissolve at 60° C. and then treated in the same manner as in Example 1 to obtain the desired product. The yield was 230 mg. The content of $PGA_2$ in the product was 8%.

EXAMPLE 5

A solution prepared by heating and dissolving 776 mg. of β-cyclodextrin in 6.6 ml. of water was added to a solution prepared by dissolving 28.8 mg. of $PGA_2$ decyl ester in 4.4 ml. of ethanol. The mixture was heated to dissolve at 60° C. and then treated in the same manner as in Example 1 to obtain the desired product. The yield was 260 mg. The content of $PGA_2$ decyl ester in the product was 10.8%.

EXAMPLE 6

A solution prepared by heating and dissolving 340 mg. of β-cyclodextrin in 4.7 ml. of water was added to a solution prepared by dissolving 27 mg. of $PGF_{2\alpha}$ in 0.3 ml. of ethanol. The mixture was heated to dissolve at 60° C. and then treated in the same manner as in Example 1 to obtain the desired product. The yield was 280 mg. The content of $PGF_{2\alpha}$ in the product was 2.6%.

EXAMPLE 7

A solution prepared by heating and dissolving 526 mg. of β-cyclodextrin in 11.8 ml. of water was added to a solution prepared by dissolving 30.73 mg. of $PGE_1$ alcohol in 0.3 ml. of ethanol. The mixture was heated to dissolve at 45° C. and then gradually cooled to the room temperature to form precipitate. After having been left standing overnight at 0° C., the precipitate was recovered by filtration and was washed with a 50% aqueous solution of ethanol and was dried under a reduced pressure to obtain 229 mg. of the desired product. The content of $PGE_1$ alcohol in the product was 6.2%.

EXAMPLE 8

A solution prepared by heating and dissolving 257 mg. of β-cyclodextrin in 6.0 ml. of water was added to a solution prepared by dissolving 16.94 mg. of α-methyl $PGE_1$ in 0.2 ml. of ethanol. The mixture was heated to dissolve at 45° C. and then treated in the same manner as in Example 7 to obtain 103 mg. of the desired product. The content of α-methyl $PGE_1$ in the product was 10.3%.

EXAMPLE 9

A solution prepared by heating and dissolving 268 mg. of β-cyclodextrin in 6.1 ml. of water was added to a solution prepared by dissolving 25.40 mg. of $PGE_2$-9-carboethoxynonyl ester in 0.3 ml. of ethanol. The mixture was heated to dissolve at 45° C. and then treated in the same manner as in Example 7 to obtain 154 mg. of the desired product. The content of $PGE_2$-9-carboethyoxynonyl ester in the product was 5.9%.

EXAMPLE 10

A solution prepared by heating and dissolving 251 mg. of β-cyclodextrin in 6.0 ml. of water was added to a solution prepared by dissolving 14.42 mg. of PG 234 in 0.2 ml. of ethanol. The mixture was heated to dissolve at 45° C. and then treated in the same manner as in Example 7 to obtain 143 mg. of the desired product. The content of PG 234 in the product was 5.5%.

EXAMPLE 11

A solution prepared by heating and dissolving 255 mg. of β-cyclodextrin in 6.0 ml. of water was added to a solution prepared by dissolving 17.37 mg. of α-methyl $PGE_2$ in 0.2 ml. of ethanol and the mixture was heated to dissolve at 45° C. and then treated in the same manner as in Example 7 to obtain 154 mg. of the desired product. The content of α-methyl $PGE_2$ in the product was 9.5%.

EXAMPLE 12

A solution prepared by heating and dissolving 165 mg. of β-cyclodextrin in 3.7 ml. of water was added to a solution prepared by dissolving 10.44 mg. of 16- methyl PGE$_2$(B) in 0.2 ml. of ethanol. The mixture was heated to dissolve at 45° C. and then treated in the same manner as in Example 7 to obtain 159 mg. of the desired product. The content of 16-methyl PGE$_2$ (B) in the product was 12.1%.

EXAMPLE 13

A solution prepared by heating and dissolving 480 mg. of β-cyclodextrin in 11.0 ml. of water was added to a solution prepared by dissolving 30.21 mg. of 17-methyl PGE$_2$(B) in 0.3 ml. of ethanol. The mixture was heated to dissolve at 45° C. and then treated in the same manner as in Example 7 to obtain 146 mg. of the desired product. The content of 17-methyl PGE$_2$ (B) in the product was 10.8%.

EXAMPLE 14

A solution prepared by heating and dissolving 490 mg. of β-cyclodextrin in 11.0 ml. of water was added to a solution prepared by dissolving 31.18 mg. of 15-methyl PGE$_2$(B) in 0.3 ml. of ethanol. The mixture was heated to dissolve at 45° C. and then treated in the same manner as in Example 7 to obtain 285 mg. of the desired product. The content of 15-methyl PGE$_2$ (B) in the product was 2.3%.

EXAMPLE 15

A solution prepared by heating and dissolving 224 mg. of β-cyclodextrin in 6.0 ml. of water was added to a solution prepared by dissolving 6.84 mg. of 16-methyl PGE$_2$(B) alcohol in 0.2 ml. of ethanol. The mixture was heated to dissolve at 45° C. and was then treated in the same manner as in Example 7 to obtain 224 mg. of the desired product. The content of 16-methyl PGE$_2$ (B) alcohol in the product was 3.0%.

EXAMPLE 16

A solution prepared by heating and dissolving 239 mg. of β-cyclodextrin in 6.0 ml. of water was added to a solution prepared by dissolving 6.95 mg. of 16-methyl PGE$_2$(B) decyl ester in 0.2 ml. of ethanol. The mixture was heated to dissolve at 45° C. and then treated in the same manner as in Example 7 to obtain 198 mg. of the desired product. The content of 16-methyl PGE$_2$ (B) decyl ester in the product was 3.0%.

EXAMPLE 17

PGE$_2$-α-cyclodextrin clathrate compound

To a solution containing 25.2 mg. PGE$_2$ dissolved in 0.3 ml. ethanol, another solution prepared separately by dissolving 510 mg. α-cyclodextrin in 2 ml. water under heating was added. The mixture was dissolved under heating to 60° C and gradually cooled to room temperature, whereupon a precipitate separated out. After being allowed to stand overnight at 0° C, the precipitate was filtered off, washed with 50% aqueous ethanol, and dried under reduced pressure to obtain 261 mg. of the desired compound. The content of PGE$_2$ in the product was 6.0%.

EXAMPLE 18

PGE$_1$ alcohole -α-cyclodextrin clathrate compound

To a solution containing 20.1 mg. PGE$_1$ alcohol dissolved in 0.2 ml. ethanol, another solution prepared separately by dissolving 418 mg. α-cyclodextrin in 2 ml. water under heating was added. The mixture was dissolved under heating to 60° C and then gradually cooled to room temperature, whereupon a precipitate separated out. After being allowed to stand overnight at 0° C, the precipitate was filtered off, washed with 50% aqueous ethanol, and dried under reduced pressure to obtain 152 mg. of the desired compound. The content of PGE$_1$ alcohol in the product was 4.1%.

EXAMPLE 19

PGE$_2$-γ-cyclodextrin clathrate compound

To a solution containing 28.3 mg. PGE$_2$ dissolved in 0.3 ml. ethanol, another solution prepared separately by dissolving 700 mg γ-cyclodextrin in 2 ml. water under heating was added. The mixture was dissolved under heating to 60° C and then gradually cooled to room temperature, whereupon a precipitate separated out. After being allowed to stand overnight at 0° C, the precipitate was filtered off, washed with 50% aqueous ethanol, and dried under reduced pressure to obtain 310 mg. of the desired compound. The content of PGE$_2$ in the product was 7.0%.

EXAMPLE 20

PGE$_1$ alcohol-γ-cyclodextrin clathrate compound

To a solution containing 22.1 mg. PGE$_1$ alcohol dissolved in 0.2 ml. ethanol, another solution prepared separately by dissolving 420 mg. γ-cyclodextrin in 1.5 ml. water was added. The mixture was dissolved under heating to 60° C and then gradually cooled to room temperature, whereupon a precipitate separated out. After being allowed to stand overnight at 0° C, the precipitate was filtered off, washed with 50% aqueous ethanol, and dried under reduced pressure to obtain 250 mg. of the desired compound. The content of PGE$_1$ alcohol in the product was 4.3%.

EXAMPLE 21

A solution prepared by heating and dissolving 248 mg. of β-cyclodextrin in 2.8 ml. of water was added to a solution prepared by dissolving 18.0 mg. of PGE$_1$ in 0.4 ml. of ethanol. The mixture was heated to dissolve at 60° C. and then treated in the same manner as in Example 1 to obtain the desired product. The yield was 203 mg. The content of PGE$_1$ in the product was 7.8%.

EXAMPLE 22

A solution prepared by heating and dissolving 253 mg. of β-cyclodextrin in 2.8 ml. of water was added to a solution prepared by dissolving 18.1 mg. of PGF$_{1\alpha}$ in 0.4 ml. of ethanol. The mixture was heated to dissolve at 60° C. and then treated in the same manner as in Example 1 to obtain the desired product. The yield was 211 mg. The content of PGF$_{1\alpha}$ in the product was 2.4%.

EXAMPLE 23

A solution prepared by heating and dissolving 240 mg. of β-cyclodextrin in 2.8 ml. of water was added to a solution prepared by dissolving 16.8 mg. of PGA$_1$ in 0.8 ml. of ethanol. The mixture was heated to dissolve at 60° C. and then treated in the same manner as in Example 1 to obtain the desired product. The yield was 183 mg. The content of PGA$_1$ in the product was 7.6%.

EXAMPLE 24

A solution prepared by heating and dissolving 240 mg. of β-cyclodextrin in 2.8 ml. of water was added to a solution prepared by dissolving 18.4 mg. of 15-methyl-PGE$_1$ in 0.4 ml. of ethanol. The mixture was heated to dissolve at 60° C. and then treated in the same manner as in Example 1 to obtain the desired product. The yield was 195 mg. The content of 15-methyl-PGE$_1$ in the product was 2.1%.

EXAMPLE 25

A solution prepared by heating and dissolving 245 mg. of β-cyclodextrin in 2.8 ml. of water was added to a solution prepared by dissolving 18.5 mg. of 16-methyl-PGE$_1$ (B) in 0.4 ml. of ethanol. The mixture was heated to dissolve at 60° C. and then treated in the same manner as in Example 1 to obtain the desired product. The yield was 170 mg. The content of 16-methyl-PGE$_1$ (B) in the product was 10.2%.

EXAMPLE 26

A solution prepared by heating and dissolving 250 mg. of β-cyclodextrin in 2.8 ml. of water was added to a solution prepared by dissolving 18.9 mg. of 17-methyl-PGE$_1$ (B) in 0.4 ml. of ethanol. The mixture was heated to dissolve at 60° C. and then treated in the same manner as in Example 1 to obtain the desired product. The yield was 168 mg. The content of 17-methyl-PGE$_1$ (B) in the product was 9.8%.

In all of the above Examples, the obtained clathrate compounds were white powdery substances and their infrared spectra showed absorptions of carbonyl groups at 1710 – 1740 cm.$^{-1}$ in the case of PGE, PGA and their analogues. The binding ratios of prostaglandins or their analogues with cyclodextrin in the clathrate compounds (i.e. content of prostaglandins or analogues thereof in the products) were determined by quantitative analysis of prostaglandins or their analogues in the clathrate compounds. The quantitative analysis was conducted in the following manner. Thus, PGA, PGE and their analogues isomerized with alkali to PGB or their analogues and their absorption values in UV spectra were determined at wavelength 278 mμ. In the case of PGF or their analogues, a contraction of guinea pig colon was employed in the determination.

It was confirmed by stability tests against heating that the clathrate compounds of this invention have excellent stabilities compared with the original prostaglandins. Table 1 shows contents of PGs or their analogues in the clathrate compounds and results of stability tests against heating at 106° ± 4° C. when cyclodextrin is used as a host molecule for prostaglandins or their analogues.

Stability tests against heating of clathrate compounds with various cyclodextrins showed excellent results regardless of the type of cyclodextrin.

Table 1

Stabilities against heat of clathrate compounds of prostaglandins or their analogues with cyclodextrin.

| Names and structures of prostaglandins or their analogues compounds | Contents*[1] | Stability against heat*[2] | | | |
|---|---|---|---|---|---|
| | | | 1 hour | 3 hours | 8 hours | 30 hours |
| PGE$_2$ | 4.7 % | PG-CD*[3] | 97.5 % | 92.8 % | 90.6 % | |
| | | PG*[4] | 77.0 | 55.0 | 29.8 | |
| PGE$_2$ decyl ester | 9.4 | PG-CD | 98.1 | 96.8 | 95.2 | |
| | | PG | 94.5 | 89.1 | 72.3 | |
| PGE$_1$ decyl ester | 7.9 | PG-CD | 99.2 | 98.5 | 97.2 | |
| | | PG | 95.2 | 89.9 | 73.4 | |
| PGA$_2$ | 8.0 | PG-CD | 99.8 | 98.8 | 98.1 | |
| | | PG | 99.4 | 98.3 | 95.6 | |

PGA$_2$ decyl ester

Table 1-continued

Stabilities against heat of clathrate compounds of prostaglandins or their analogues with cyclodextrin.

| Names and structures of prostaglandins or their analogues compounds | Contents[*1] | Stability against heat[*2] | | | | |
|---|---|---|---|---|---|---|
| | | | 1 hour | 3 hours | 8 hours | 30 hours |
| 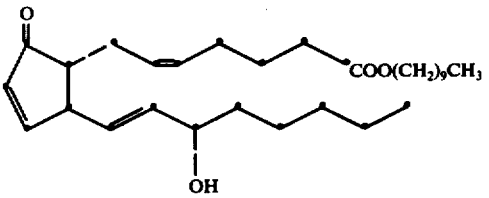 | 10.8 | PG-CD<br>PG | 99.8<br>99.5 | 99.2<br>98.6 | 98.6<br>97.0 | |
| $PGF_{2\alpha}$<br>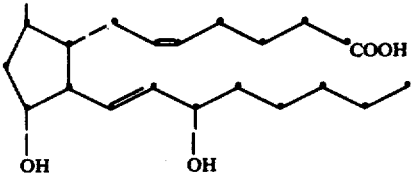 | 2.6 | PG-CD<br>PG | 100<br>100 | 100<br>99 | 99<br>99 | |
| $PGE_1$ alcohol<br>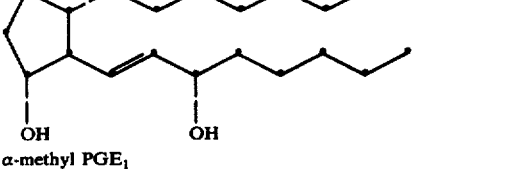 | 6.2 | PG-CD[*3]<br>PG[*4] | 92.9<br>95.4 | 92.8<br>93.8 | 88.0<br>84.9 | 79.1 %<br>59.8 |
| α-methyl $PGE_1$<br>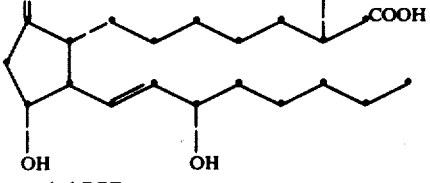 | 10.3 | PG-CD<br>PG | 97.4<br>82.1 | 88.5<br>69.2 | 90.5<br>55.2 | |
| α-methyl $PGE_2$<br>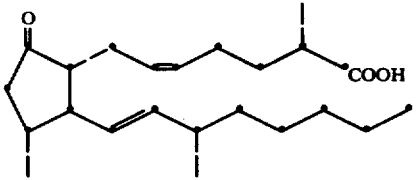 | 9.5 | PG-CD<br>PG | 96.6<br>94.4 | 92.5<br>69.1 | 91.9<br>61.7 | |
| PG 234<br>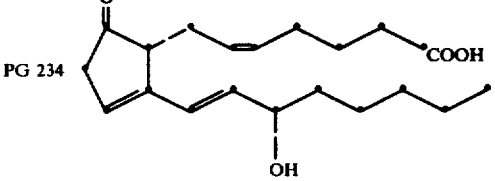 | 5.6 | PG-CD<br>PG | 96.3<br>54.9 | 96.3<br>48.8 | 95.6<br>46.0 | |
| $PGE_2$-9-carbo-ethoxy nonyl ester<br>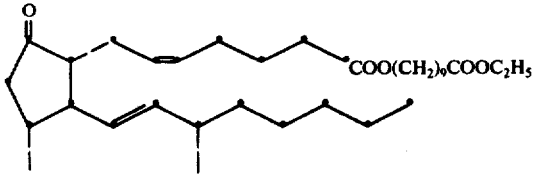 | 5.9 | PG-CD<br>PG | 100.0<br>97.5 | 96.4<br>93.8 | 97.3<br>90.8 | 94.2<br>69.6 |
| 16-methyl $PGE_2$ (B) | | | | | | |

Table 1-continued

Stabilities against heat of clathrate compounds of prostaglandins or their analogues with cyclodextrin.

| Names and structures of prostaglandins or their analogues compounds | Contents*[1] | | Stability against heat*[2] | | | |
|---|---|---|---|---|---|---|
| | | | 1 hour | 3 hours | 8 hours | 30 hours |
| 17-methyl PGE$_2$ (B) | 12.1 | PG-CD | 97.8 | 92.1 | 87.9 | |
| | | PG | 75.9 | 62.9 | 45.6 | |
| 15-methyl PGE$_2$ | 10.8 | PG-CD | 98.7 | 97.9 | 97.4 | |
| | | PG | 76.9 | 66.7 | 59.9 | |
| 16-methyl PGE$_2$ (B) alcohol | 2.3 | PG-CD | 86.8 | 86.5 | 83.4 | |
| | | PG | 65.4 | 49.4 | 43.6 | |
| 16-methyl PGE$_2$ (B) decyl ester | 3.0 | PG-CD | 98.7 | 90.9 | 91.9 | |
| | | PG | 84.4 | 66.2 | 63.0 | |
| | 3.0 | PG-CD | 94.1 | 87.0 | 85.6 | |
| | | PG | 85.6 | 70.2 | 64.7 | |

| | | | Heat stability | | | |
|---|---|---|---|---|---|---|
| | | | 1 hr | 3 hr | 8 hr | 30 hr |
| PGE$_2$ | PGE$_2$ | | 77.0 | 55.0 | 29.8 | |
| | PGE$_2$-α-CD | 6.0 | 97.0 | 92.2 | 89.5 | |
| | PGE$_2$-γ-CD | 4.1 | 97.3 | 92.0 | 90.1 | |
| PGE$_1$ alcohol | PGE$_1$ alcohol | | 95.4 | 93.8 | 84.9 | 59.8 |
| | PGE$_1$ alcohol-α-CD | 7.0 | 92.1 | 91.8 | 87.5 | 77.6 |
| | PGE$_1$ alcohol-γ-CD | 4.3 | 93.4 | 92.5 | 88.6 | 78.4 |
| PGF$_{1α}$ | | 2.3 | PG-CD*[3] 100 | 100 | 99 | |
| | | | PG*[4] 100 | 99 | 99 | |

Table 1-continued

Stabilities against heat of clathrate compounds of prostaglandins or their analogues with cyclodextrin.

| Names and structures of prostaglandins or their analogues compounds | Contents[*1] | Stability against heat[*2] | | | |
|---|---|---|---|---|---|
| | | | 1 hour | 3 hours | 8 hours 30 hours |
| PGA$_1$ | 7.6 | PG-CD<br>PG | 99.8<br>99.5 | 98.8<br>98.3 | 98.0<br>95.0 |
| PGE$_1$ | 7.8 | PG-CD<br>PG | 98.0<br>80.2 | 91.2<br>57.2 | 90.3<br>28.2 |
| 15-methyl PGE$_1$ | 2.1 | PG-CD<br>PG | 88.2<br>68.0 | 87.8<br>48.3 | 84.0<br>40.6 |
| 16-methyl PGE$_1$(B) | 10.2 | PG-CD<br>PG | 96.5<br>73.2 | 92.0<br>63.5 | 86.2<br>48.0 |
| 17-methyl PGE$_1$ (B) | 9.8 | PG-CD<br>PG | 97.8<br>75.3 | 97.5<br>68.2 | 97.0<br>61.2 |

[*1] The contents are represented by percentages (w/w) of prostaglandins or their analogues in the clathrate compounds.
[*2] The percentages of prostaglandins or their analogue compounds remaining stable at 106° ± 4° C.
[*3] In the table, PG-CD represents cyclodextrin clathrate compounds of prostaglandins or their analogues.
[*4] In the table, PG represents prostaglandins or their analogues.

As shown in Table 1, there is a great variety in contents of prostaglandins or their analogues in the clathrate compounds according to structures of the compounds. With regard to stabilities to heating, the clathrate compounds are shown to be much more stable than the original prostaglandins or their analogues. Such stable prostaglandins have never been known up to the present. It would be significant in this respect that, according to the invention, the cyclodextrin clathrate compounds first permitted the use of prostaglandins in pharmaceutical forms. Since all the obtained clathrate compounds are white powders and so easy to deal with, they are very useful in various pharmaceutical forms such as injection, tablets, capsule, suspension, aerosol, powder and the like.

The following examples illustrate come procedures for making the clathrate compounds of this invention into pharmaceutically useful forms.

EXAMPLE 27

PGE$_2$-cyclodextrin Tablet for Vagina

| | |
|---|---|
| Avicel (micro crystalline cellulose) | 10 g. |
| Mannite | 12.5 g. |
| Tartaric acid | 10 g. |

| | |
|---|---|
| Sodium bicarbonate | 10 g. |
| ECG 505 (Carboxy methyl cellulose-calcium) | 2 g. |

Granules are made by mixing well the above ingredients and adding to the mixture 0.5 g. of PVP (polyvinylpyrrolidone) dissolved in a small amount of methanol as a binder. After dried satisfactorily, the granules were passed through the 12 mesh sieve to obtain uniform size granules. To these granules were added the following ingredients:

| | |
|---|---|
| $PGE_2$-CD (PG content 8%) | 2.5 g. |
| ECG 505 (carboxymethyl cellulose-calcium) | 2 g. |
| Magnesium stearate | 0.5 g. |

Effervescent tablets for vagina containing 2 mg. of $PGE_2$ in each tablet were obtained by tableting the mixture into tablets each 500 mg. of weight.

EXAMPLE 28

$PGE_2$-cyclodextrin tablet

Granules were made by mixing well 17.5 g. of lactose and 3.89 g. of starch and adding HPC (hydroxy propyl cellulose) in 0.5 g. of methanol as a binder. After dried satisfactorily, they are sieved through the 12 mesh sieve to obtain uniform size granules. After adding to the granules 2.86 g. of $PGE_2$-cyclodextrin (PG content 7%) and 250 mg. of magnesium stearate, tablets are made, each being 8.5 mm. in diameter and 250 mg. in weight. Each tablet contained 2 mg. of $PGE_2$.

EXAMPLE 29

$PGE_2$ decyl ester-cyclodextrin capsule

| | |
|---|---|
| $PGE_2$ decyl ester-cyclodextrin (PG content 9.4%) | 0.43 g. |
| Mannite | 3 g. |
| Corn starch | 0.4 g. |

The above agents were mixed well and sieved through 32-mesh sieve several times. After that, 220 mg. of the mixture was packed in each No. 3 hard capsule. Each capsule contained 2 mg. of $PGE_2$ decyl ester.

EXAMPLE 30

$PGE_2$-cyclodextrin Injection

Powdery $PGE_2$-cyclodextrin (PG content 8%) was subdivided into ampoules so that each contains 12.5 mg. under sterile condition. Each ampoule was substituted by nitrogen gas and sealed. This was useful as an injection containing 1 mg. of $PGE_2$ when dissolved in a 0.9% saline solution for injection.

EXAMPLE 31

$PGF_{2\alpha}$-Cyclodextrin Powder

| | |
|---|---|
| $PGF_{2\alpha}$-cyclodextrin (PG content 2%) | 20 g. |
| Potato starch | 90 g. |

The above ingredient were mixed well and sieved through 42-mesh sieve. Then 400 g. of lactose were added to the mixture and the mixture was sieved again through 42-mesh sieve. Further, they were mixed to obtain 0.1% $PGF_{2\alpha}$ powder.

When this invention is practically applied to pharmaceutical uses, it is also possible to make a pharmaceutical preparation comprising a mixture of the clathrate compounds of prostaglandins or their analogues with cyclodextrin and free cyclodextrin left by using an excess of cyclodextrin in the reaction with prostaglandins or their analogues.

The biological activities of the clathrate compounds of this invention, that is to say, hypotensive effects, contractive effects of uterine or intestinal smooth muscle, gastric secretion inhibiting effects or the like, were almost similar to those of the original prostaglandins or their analogues. And the toxicity of the cyclodextrin is so low that if intravenously injected to male mice at a dosage of more than 1 g./kg., none of them die. Consequently there is no obstacle in the application of these clathrate compounds to medical use.

As explained above the clathrate compounds of this invention are useful as various therapeutic preparations in various pharmaceutical forms. The administrative dosage may vary over a wide range depending upon particular prostaglandin compound used, particular manner of administration, particular pharmaceutical form and particular disease to be treated. The following examples illustrate some typical actual uses of the agents.

LABOR-INDUCING AGENTS

A labor-inducing agent in the form of vagina tablet, tablet, capsule or powder containing $PGE_2$-cyclodextrin may be administered in a total amount of 60 – 120 mg. (as $PGE_2$-cyclodextrin) as divided into 3 – 6 times with an interval of about 2 – 3 hours. A vagina tablet is inserted in the vagina, while tablet, capsule or powder is administered orally. In case of infusion, the administration is conducted for a long time and in an amount of 5 – 30 mg.

$PGF_{2\alpha}$-cyclodextrin may be administered in the same manner except that the total dosage in the form of vagina tablet, tablet, capsule or powder is 250 mg. – 5 g., while in the case of infusion it is 100 mg. – 1 g.

CONTRACEPTIVE

A contraceptive agent in the form of vagina tablet, tablet, capsule or powder containing $PGE_2$-cyclodextrin may be administered in a total amount of 200 mg. to 1.2 g. (as $PGE_2$-cyclodextrin) as divided into 2 – 3 times with an interval of about 2 – 3 hours. A vagina tablet is inserted in the vagina, while tablet, capsule or powder is administered orally. In case of infusion, the administration is conducted for a long time with a total dosage of 20 mg. – 150 mg.

$PGF_{2\alpha}$-cyclodextrin may be administered in the same manner except that the total dosage in the form of vagina tablet, tablet, capsule or powder is 1 – 8 g. while in the case of infusion it is 500 mg. – 5 g.

Remedy for ulcer

For remedy for ulcer, $PGE_2$-cyclodextrin in the form of tablet, capsule or powder may be continuously and orally administered with a dosage of 5 – 50 mg. (as $PGE_2$-cyclodextrin)/day/adult.

$PGE_2$ decylester-cyclodextrin may be administered in the same manner except that the dosage is 40 – 400 mg./day/adult.

Hypotensive agent

As hypotensive agent, $PGE_2$-cyclodextrin in the form of tablet, capsule or powder may be administered orally in an amount of 2.5 – 25 mg. (as PGE$_2$-cyclodextrin). In case of intramuscular injection the dosage may be 1 – 10 mg.

PGA$_2$ decylester-cyclodextrin may be administered orally in the same manner except that the dosage is 20 – 200 mg.

Remedy for asthma

For remedy for asthma, an aerosal agent containing PGE$_1$ alcohol-cyclodextrin and/or PGE$_2$-9-carboethoxynonylestercyclodextrin may be sprayed in an amount of 100 µg. to 500 µg. (as the clathrate compound) at a time.

The pharmacological activities of the various prostaglandin clathrate compounds are as follows:

I. Pharmacological activities:

The following are pharmacological activities of prostaglandin clathrate compounds.

i. Hypotensive activity:

Hypotensive activity and duration of various prostaglandin-CD compounds were compared with those of PGE$_2$-CD in allobarbital anesthetized dogs, the activity of the latter being take as 100%.

| (intravenous administration) PG-CD | content* | activity | duration |
|---|---|---|---|
| PGE$_2$-CD | 4.7% | 100% | 7 min. |
| PGE$_2$decyl ester-CD | 9.4 | 10 | 50 |
| PGE$_1$-CD | 7.8 | 160 | 7 |
| PGE$_1$ decyl ester-CD | 7.9 | — | <60 |
| PGA$_2$-CD | 8.0 | 1000 | 7 |
| PGA$_2$ decyl ester-CD | 10.8 | 1 | 50 |
| PGF$_{2\alpha}$-CD | 2.6 | — | — |
| PGF$_{1\alpha}$-CD | 2.3 | — | — |
| PGA$_1$-CD | 7.6 | 1000 | 7 |
| PGE$_1$alcohol-CD | 6.2 | 30 | 20 |
| αMe PGE$_1$-CD | 10.3 | 10 | 4 |
| αMePGE$_2$-CD | 9.5 | 5 | 2 |
| PG$_{234}$-CD | 5.6 | 250 | 12 |
| PGE$_2$ 9-carboethoxy nonyl ester-CD | 5.9 | 75 | 13 |
| 15MePGE$_2$-CD | 2.3 | 25 | 93 |
| 16MePGE$_2$(B)-CD | 12.1 | 800 | 17 |
| 17MePGE$_2$(B)-CD | 10.8 | 200 | 2 |
| 15MePGE$_1$-CD | 2.1 | 50 | 50 |
| 16MePGE$_1$(B)-CD | 10.2 | 800 | 12 |
| 17MePGE$_1$(B)-CD | 9.8 | 500 | 4 |
| 16MePGE$_2$(B)alcohol-CD | 3.0 | 40 | 51 |
| 16MePGE$_2$(B)decyl ester-CD | 3.0 | 20 | 70 |

*content percentage (W/W) of prostaglandin compound in β-cyclodextrin clathratecompound.

ii. Platelet aggregation inhibitory activity:

According to the method of Born et al. (J. Physiol. 168, 178 (1963)), platelet aggregation inhibitory activities of various prostaglandin CD compounds were determined with the platelet aggregation in rabbits' platelet rich plasma (PRP) caused by administration of ADP (6 γ/ml). Administration amounts of PG-CD were shown in terms of molar concentration of prostaglandin included.

| PG-CD | Administration amount M | Platelet aggreg. inhibitory percent. (%) |
|---|---|---|
| PGE$_2$-CD | 2.8 × 10$^{-8}$ | 44.0 |
| PGE$_2$decyl ester-CD | 2.4 × 10$^{-4}$ | 86.2 |
| PGE$_1$-CD | 2.8 × 10$^{-10}$ | 98.1 |
| PGE$_1$decyl ester-CD | 2.0 × 10$^{-6}$ | 60.4 |
| PGE$_1$alcohol-CD | 2.9 × 10$^{-5}$ | 40.0 |
| αMePGE$_1$-CD | 2.7 × 10$^{-6}$ | 55.0 |
| 15MePGE$_1$-CD | 2.7 × 10$^{-5}$ | 68.4 |
| 16MePGE$_1$(B)-CD | 2.7 × 10$^{-8}$ | 74.9 |
| 17MePGE$_1$(B)-CD | 1.1 × 10$^{-10}$ | 95.2 |

As shown above, all of the present prostaglandin clathrate compounds (PG-CD) possessed almost the same high order of hypotensive activity and platelet aggregation inhibitory activity as possessed by the original prostaglandins used in making the same.

When these PG-CD compounds were given at a level of 2 mg/kg calculated in terms of prostaglandin to spayed rats for evaluation of their gastric secretion inhibitory activities, PGE$_2$ decyl ester-CD and PGE$_1$ decyl ester-CD showed 71% and 55% activities of that of original prostaglandin compounds respectively, and 16MePGE$_1$(B)-CD showed 100 – 200 times activities of that of PGE$_1$ decyl ester-CD.

When examined with stress ulcer rats at a dosage of 200 µg/kg calculated in terms of prostaglandin, 15Me PGE$_1$-CD showed 87% inhibitory percentage.

When examined with histamins induced bronchial contraction in anesthetized guinea pigs, PGE$_1$-CD showed the same activity with that of Isoproterenol, and 16MePGE$_1$-(B)-CD showed even a higher activity and longer durability.

When examined with extracted uterus muscle contraction in rats, PGF$_{1\alpha}$-CD and PGF$_{2\alpha}$-CD showed 50% contraction at a level of 8.5 × 10$^{-9}$ g/ml calculated in terms of prostaglandin.

From the foregoing, it is apparent that each PG-CD compound possesses almost the same level of pharmacological activities and effects with those of the original prostaglandin.

II. Blood flow increasing activity of PGE$_1$-CD:

1. When PGE$_1$-CD was administrated to the dogs anesthelized with allobarbital, the blood flow was observated by means of electromagnetic flow meter, on the following three arteries.

PGE$_1$-CD caused increase of blood flow on these arteries as the following table.

| Artery | Dose | Route of administration | Increasing amount of blood flow |
|---|---|---|---|
| fermoral artery | 0.1–0.5 ng/kg | intraarterial injection | detectable increase |
|  | 1–2 ng/kg | " | 50–100 % |
|  | 0.07–0.5 ng/kg/min. | intraarterial infusion | 15–50 % |
|  | 1–5 µg/kg | intravenous injection | 30–40 % |
| Interal carotid artery | 1–10 ng/kg | intraarterial injection | 30–100% |
| Coronary artery | 10–100 ng/kg | intraarterial injection | 30–100 % |

2. Clinical:

i. Thromboangities obliterans:

When PGE$_1$-CD was administrated intravenously by injection at the dose of 0.5 µg/kg to the patient with thromboangitis obliterans, PGE$_1$-CD caused improvement of the pulse wave and increase of the cardiac minute volume.

ii. Buerger's disease:

In the case of Buerger's disease, PGE$_1$-CD was administrated intraarterially by infusion at the dose of 0.1 – 1 ng/kg/min. for 6 hours, PGE$_1$-CD brought the decrease of plane gangrene, appearance of dicrotic wave in pulse and decrease of pain.

What is claimed is:

1. A cyclodextrin clathrate compound of a prostaglandin having the structure:

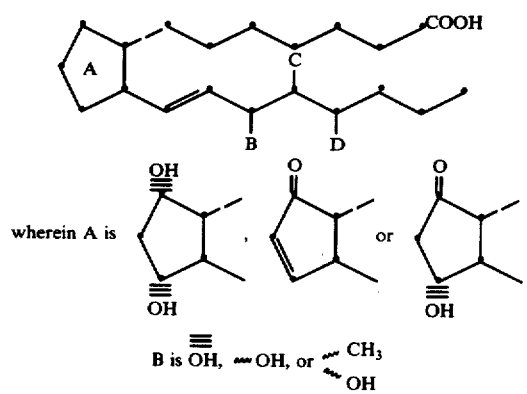

and C and D are each hydrogen or —CH$_3$.

2. The clathrate compound of claim 1 in which the compound is PGE$_1$ cyclodextrin clathrate.

3. The clathrate compound of claim 1 in which the compound is PGE$_{1\alpha}$ cyclodextrin clathrate.

4. The clathrate compound of claim 1 in which the compound is PGA$_1$ cyclodextrin clathrate.

5. The clathrate compound of claim 1 in which the compound is 15-methyl PGE$_1$ cyclodextrin clathrate.

6. The clathrate compound of claim 1 in which the compound is 16-methyl PGE$_1$(B) cyclodextrin clathrate.

7. The clathrate compound of claim 1 in which the compound is 17-methyl PGE$_1$(B) cyclodextrin clathrate.

8. The clathrate compound of claim 1, in which the cyclodextrin is α-, β-, γ-cyclodextrin.

9. The clathrate compound of claim 8 in which the cyclodextrin is α-cyclodextrin.

10. The clathrate compound of claim 8, in which the cyclodextrin is β-cyclodextrin.

11. The clathrate compound of claim 8 in which the cyclodextrin is γ cyclodextrin.

12. Clathrate compound of prostaglandins or their analogs with α- cyclodextrin.

13. Clathrate compounds of prostaglandins or their analogs with β-cyclodextrin.

14. Clathrate compounds of prostaglandins or their analogs with γ-cyclodextrin.

15. The clathrate compound of claim 12 in which the prostaglandins or their analogs are selected from the group consisting o PGE$_2$ and PGE$_1$ alcohol.

16. The clathrate compounds of claim 13 in which the prostaglandins or their analogs are selected from the group consisting of PGA$_1$, PGA$_2$, PGA$_2$-decyl ester, PGE$_1$, PGE$_1$ alcohol, PGE$_1$- decyl ester, α-methyl-PGE$_1$, 15-methyl-PGE$_1$, 16-methyl-PGE$_1$(B), 17-methyl-PGE$_1$(B), PGE$_2$, PGE$_2$-decyl ester, α-methyl PGE$_2$, 15-methyl-PGE$_2$ (B), 16-methyl-PGE$_2$ (B), 17-methyl-PGE$_2$(B), 16-methyl-PGE$_2$ (B)-decyl ester, 16-methyl-PGE$_2$(B) alcohol, PGE$_2$-9-carboethoxynonyl ester, PGF$_{1\alpha}$, PGF$_{2\alpha}$ and PG 234.

17. The clathrate compounds of claim 14 in which the prostaglandins or their analogs are selected from the group consisting of PGE$_2$ and PGE$_1$ alcohol.

18. A pharmaceutical composition which comprises a clathrate compound of prostaglandin or its analog with cyclodextrin, in which the cyclodextrin is α-, β-, or γ-cyclodextrin, and a pharmaceutically acceptable carrier.

19. The pharmaceutical composition of claim 18 in which the cyclodextrin is α-cyclodextrin.

20. The pharmaceutical composition of claim 18 in which the cyclodextrin is β-cyclodextrin.

21. The pharmaceutical compositions of claim 18 in which the cyclodextrin is γ-cyclodextrin.

* * * * *